US00PP28948P2

(12) United States Plant Patent
van Langen

(10) Patent No.: US PP28,948 P2
(45) Date of Patent: Feb. 6, 2018

(54) ***ALOE* PLANT NAMED 'AMIAL1614'**

(50) Latin Name: *Aloe aristata*
Varietal Denomination: AMIAL1614

(71) Applicant: NovoAmi B.V., Heerhugowaard (NL)

(72) Inventor: Gerard van Langen, Heerhugowaard (NL)

(73) Assignee: NovoAmi B.V., Heerhugowaard (NL)

( * ) Notice: Subject to any disclaimer, the term of this patent is extended or adjusted under 35 U.S.C. 154(b) by 0 days.

(21) Appl. No.: 15/530,563

(22) Filed: Jan. 30, 2017

(51) Int. Cl.
*A01H 5/12* (2006.01)

(52) U.S. Cl.
USPC ..... Plt./373

(58) Field of Classification Search
USPC ..... Plt./373, 372
CPC ..... A01H 5/12; A01H 5/02; A01H 5/00
See application file for complete search history.

*Primary Examiner* — Kent L Bell
(74) *Attorney, Agent, or Firm* — Samuel R. McCoy, Jr.

(57) ABSTRACT

A new and distinct *Aloe aristata* cultivar named 'AMIAL1614' which is characterized by erect foliage arranged in a basal rosette, dark green foliage which is densely covered with large white papillae and prominent spines along the margins, papillae on the abaxial leaf surface which are arranged in distinct transverse rows, and the stability of these characteristics from generation to generation.

4 Drawing Sheets

Latin name of the genus and species: The Latin name of the genus and species of the novel variety disclosed herein is *Aloe aristata*.

Variety denomination: The inventive variety of *Aloe* disclosed herein has been given the variety denomination 'AMIAL1614'.

BACKGROUND OF THE INVENTION

Parentage: 'AMIAL1614' is a seedling selection resulting from the self-pollination of the species, *Echeveria agavoides* (unnamed unpatented plant). The crossing was made by the inventor in the autumn of 2011 at a commercial greenhouse in Heerhugowaard, the Netherlands. Seed from said cross was harvested, then germinated, and the resulting seedlings were then grown to a mature size. In summer of 2013, 'AMIAL1614' was selected for commercialization due to its unique foliage characteristics and growth habit.

Asexual Reproduction: Asexual reproduction of the new cultivar 'AMIAL1614', by way of rooting leaf cuttings, was first initiated in the summer of 2015 at the inventor's commercial greenhouse in Heerhugowaard, the Netherlands. The claimed plant has since been asexually propagated by way of meristematic tissue culture propagation. Through three subsequent generations, the unique features of this cultivar have proven to be stable and true to type.

SUMMARY OF THE INVENTION

The cultivar 'AMIAL1614' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'AMIAL1614'. These characteristics in combination distinguish 'AMIAL1614' as a new and distinct *Aloe aristata* cultivar:

1. 'AMIAL1614' exhibits erect foliage arranged in a basal rosette; and
2. 'AMIAL1614' exhibits dark green foliage which is densely covered with large, prominent papillae on both the adaxial and abaxial surfaces, and large prominent spines along the margins; and
3. 'AMIAL1614' exhibits large papillae which are colored white, and occasionally bearing spines; and
4. 'AMIAL1614' exhibits papillae on the abaxial leaf surface which are arranged in distinct transverse rows.

BOTANICAL DESCRIPTION OF THE PLANT

Figure 1:
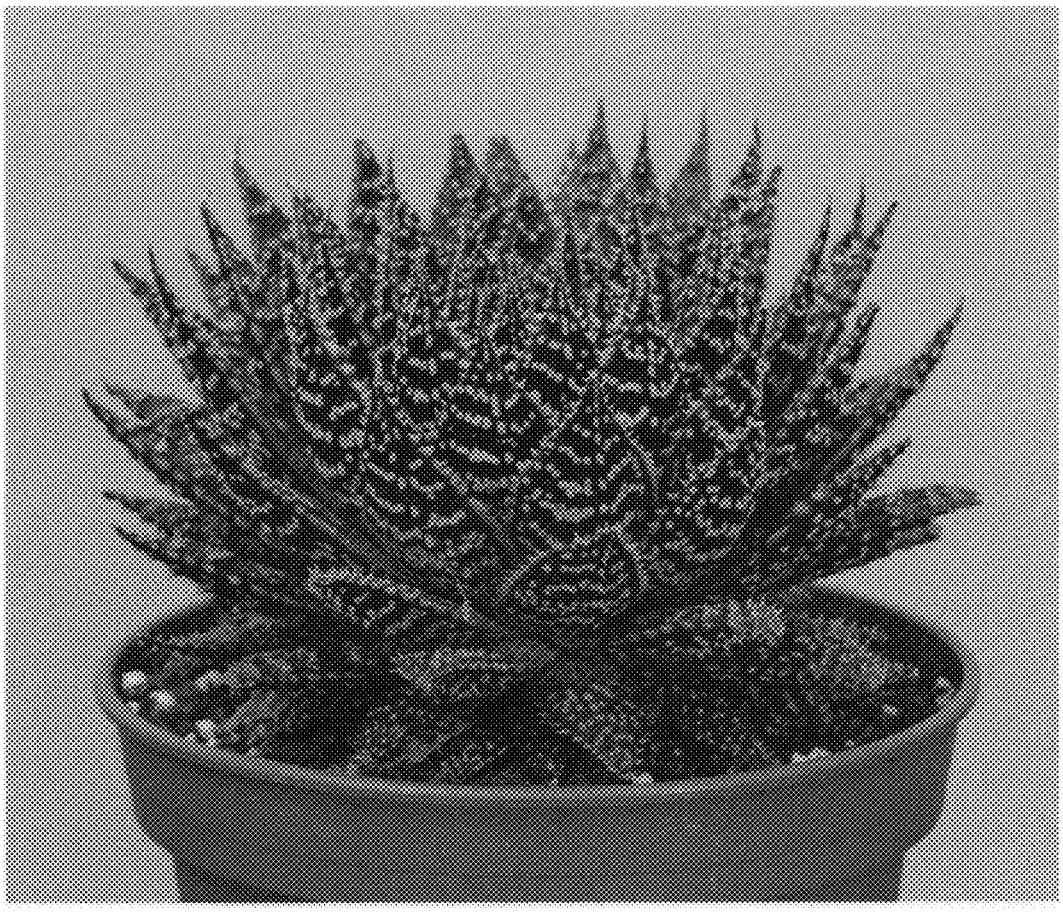
FIG. 1 illustrates, as nearly true as it is reasonably possible to make the same in color photographs of this type, an exemplary plant of 'AMIAL1614' grown in a commercial greenhouse in Heerhugowaard, the Netherlands. This plant is approximately 9 months old, shown planted in a 12 cm container.
Figure 2:
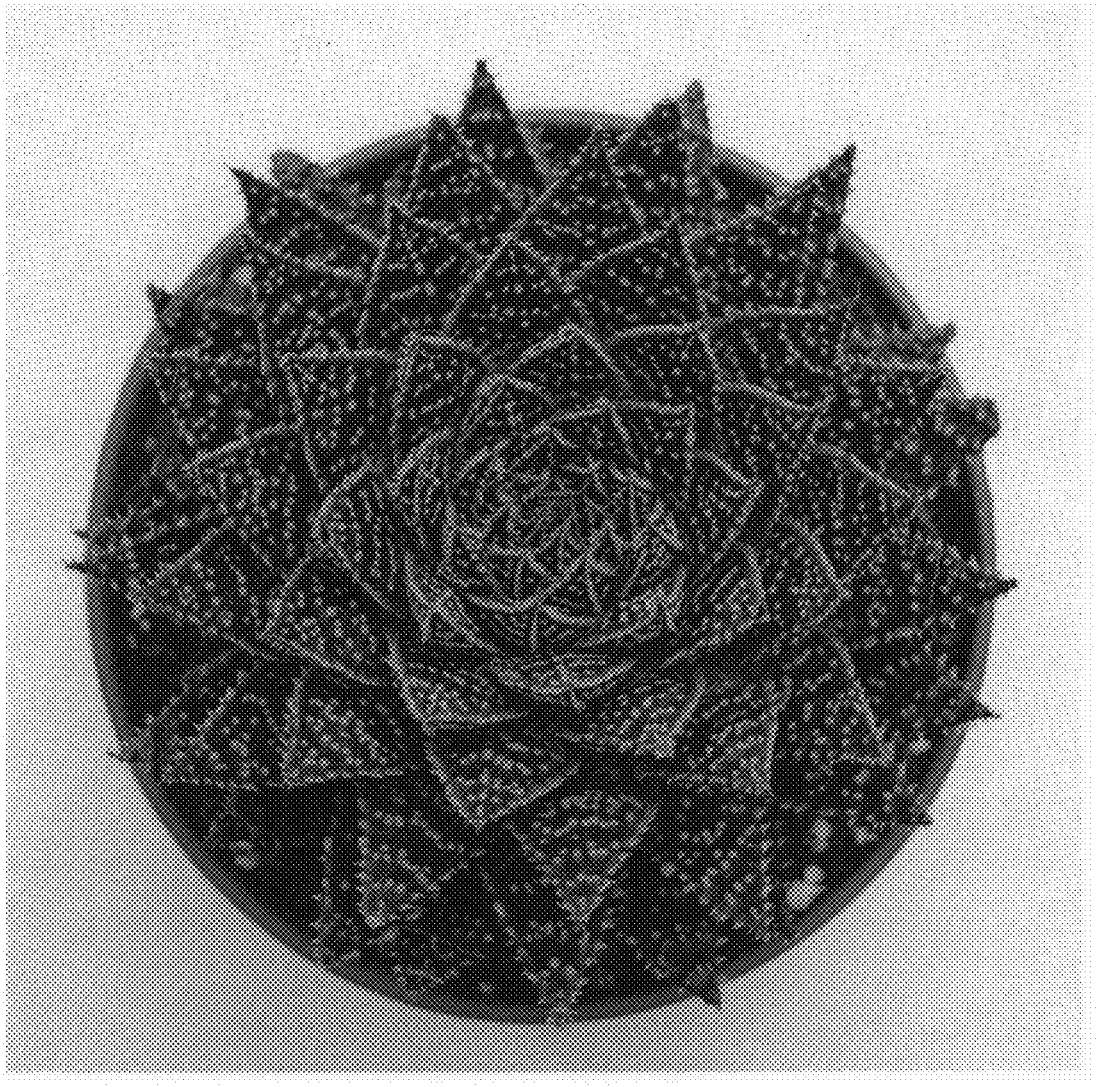
FIG. 2 illustrates, as nearly true as it is reasonably possible to make the same in color photographs of this type, the typical foliage arrangement of 'AMIAL1614'.
Figure 3:
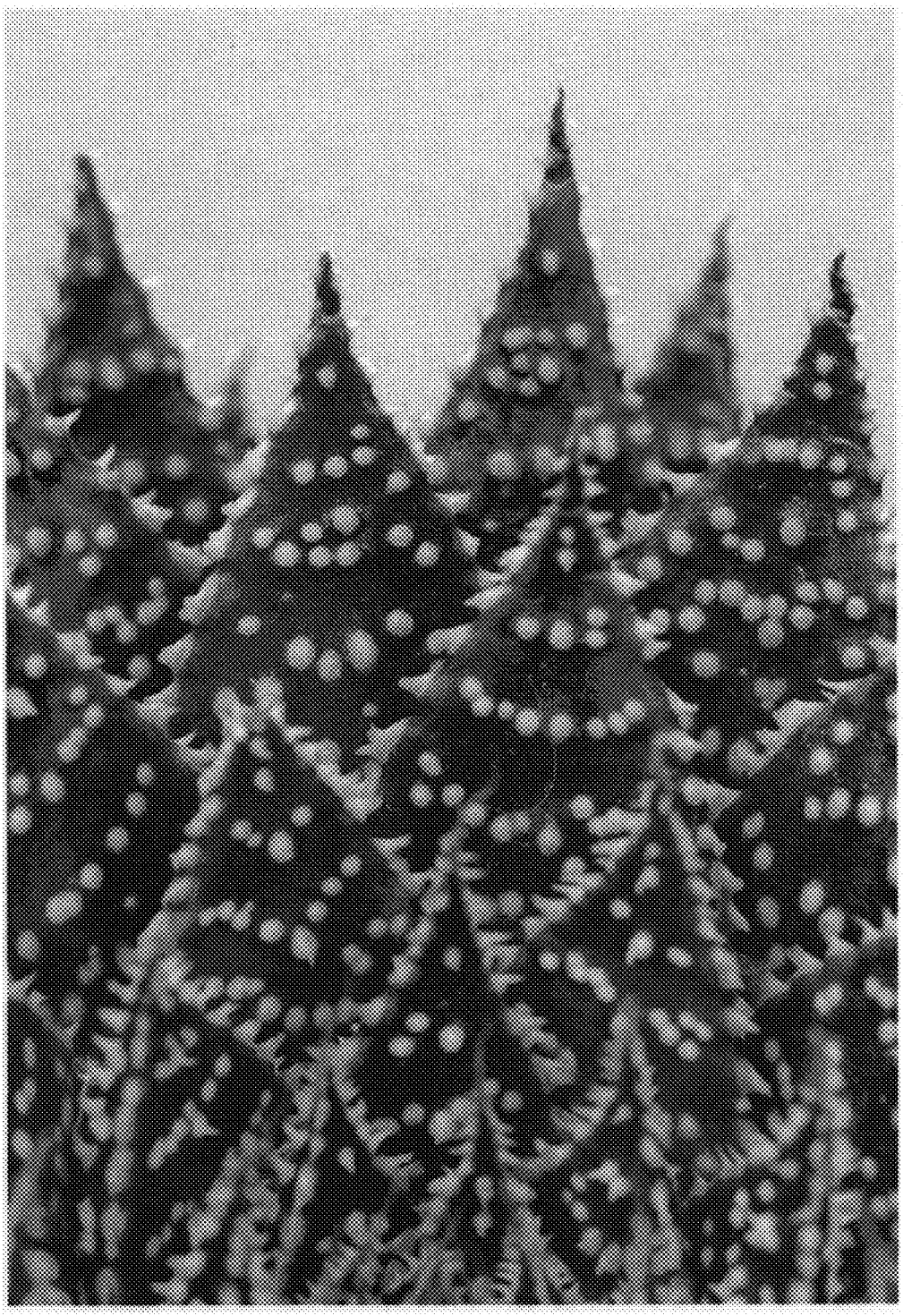
FIG. 3 illustrates, as nearly true as it is reasonably possible to make the same in color photographs of this type, the adaxial surface of the mature foliage 'AMIAL1614'.
Figure 4:
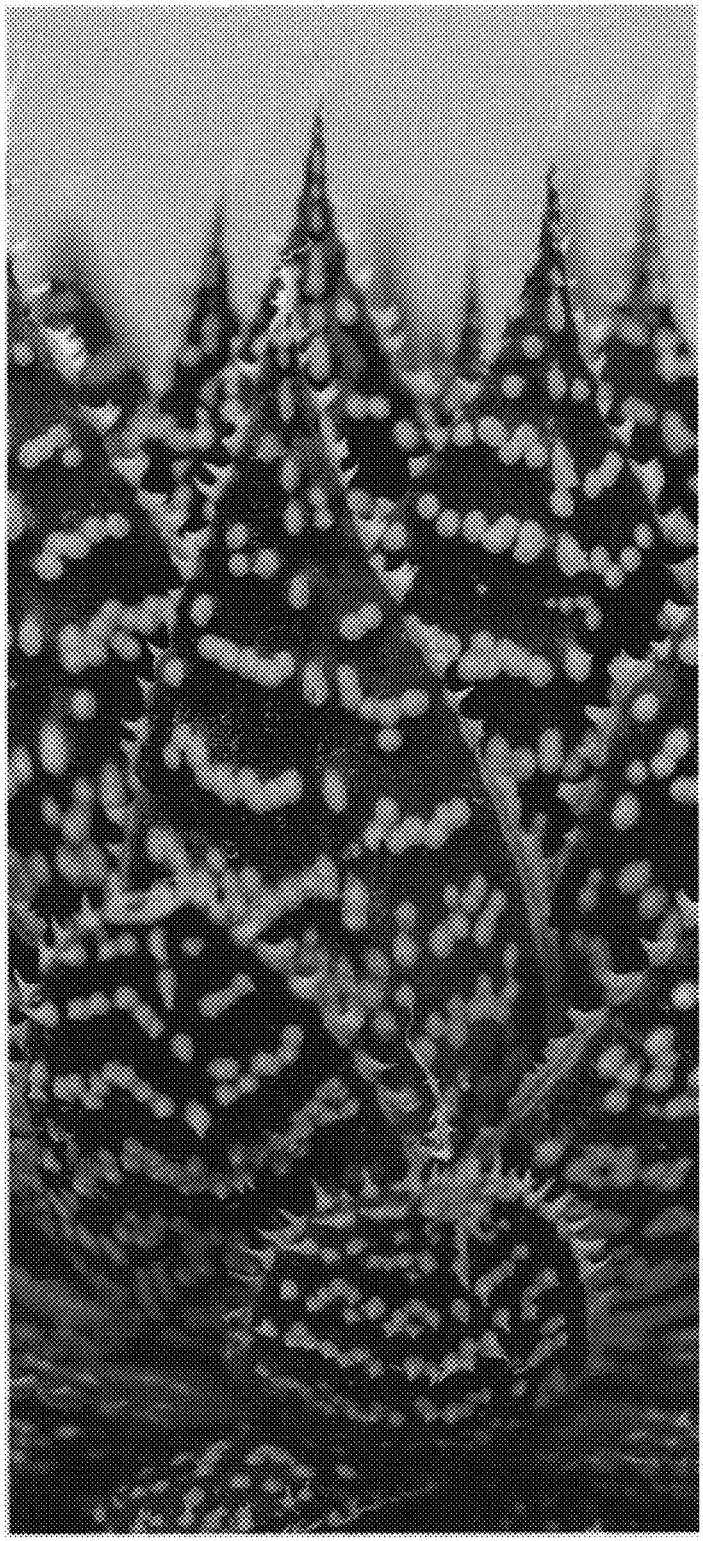
FIG. 4 illustrates, as nearly true as it is reasonably possible to make the same in color photographs of this type, the abaxial surface of the mature foliage 'AMIAL1614'.

The following observations and measurements made in October of 2016 describe averages from a sample set of six specimens of 9 months old 'AMIAL1614' plants grown in 11 cm nursery containers at commercial greenhouse in Heerhugowaard, The Netherlands. Plants were produced using conventional greenhouse production protocols for *Aloe* which consisted of minimal irrigation and fertilizer applications, and chemical pest and disease control measures against mealy bug and *Botrytis* as required. Plants were grown under approximately 50 percent shade and no photoperiodic treatments or artificial light was given to the plants.

Those skilled in the art will appreciate that certain characteristics will vary with older or, conversely, with younger plants. 'AMIAL1614' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions. Color notations are based on *The Royal Horticultural Society Colour Chart*, The Royal Horticultural Society, London, 2015 (sixth edition).

A botanical description of 'AMIAL1614' and a comparison with the parent and closest known comparator is provided below.

Plant description:

*Growth habit*.—Succulent perennial with foliage growing in a non-branched basal rosette.

*Plant shape*.—Globular to flattened globular.

*Height from soil level to top of foliar plane*.—11.5 cm.

*Plant spread*.—Average of 15.3 cm.

*Growth rate*.—Low to moderate.

*Plant vigor*.—Low to moderate.

*Propagation*.—Type — Leaf cuttings and meristematic tissue culture. Time to initiate rooting — Approximately 28 to 35 days at 18 degrees Celsius. Crop time — Approximately 18 to 22 weeks to produce a marketable plant in a 7 cm container.

*Disease and pest resistance or susceptibility*.—Neither resistance nor susceptibility to typical *Aloe aristata* pests and diseases has been observed.

*Environmental tolerances*.—Adapt to, at least, USDA Zones 10 to 12 and temperatures as high as 40 degrees Celsius; low tolerance to rain; high tolerance to wind.

Root system:

*General*.—Fine, well-branched fibrous roots.

Stems:

*Branching habit*.—Leaves in a non-branching basal rosettes; no main branches or lateral branches present.

Foliage:

*Arrangement*.—Rosette.

*Division*.—Simple.

*Attachment*.—Sessile.

*Quantity*.—Approximately 120 leaves per rosette.

*Shape*.—Thick, succulent leaves which are narrow triangular to narrow ovate.

*Dimensions*.—6.8 cm long, 2.6 cm wide, and 0.9 cm thick, on average.

*Aspect*.—Flat to very slightly concaved.

*Attitude*.—Erect.

*Apex*.—Narrow acute with a caudate tip.

*Base*.—Broad cuneate.

*Margin*.—Dentate; not undulated or lobed.

*Texture, adaxial surface*.—Glabrous and moderately covered with large orbicular papillae, each approximately 1.5 mm high and 1.5 mm in diameter; papilla occasionally bearing spines.

*Texture, abaxial surface*.—Glabrous and covered with large oblong papillae, more or less arranged in transverse rows; each papilla approximately 2.0 mm high and 1.5 mm in diameter; papilla occasionally bearing spines.

*Luster, adaxial surface*.—Slightly glossy.

*Luster, abaxial surface*.—Slightly glossy.

*Color*.—Juvenile foliage, adaxial surface — Green, nearest to RHS NN137A, and fading to yellow-green towards the base, nearest to RHS 144C; papillae are colored in between white, RHS N155A, and green-white, in between RHS 157C and 157D. Juvenile foliage, abaxial surface — Green, nearest to RHS 141A, and fading to yellow-green towards the base, nearest to RHS 144C; papillae are colored white, nearest to RHS N155A. Mature foliage, adaxial surface — Green, nearest to RHS NN137A, and lightly suffused with greyed-green, nearest to RHS 189A; suffused with a darker shade of greyed-green towards the base, in between RHS 194A and 194B; papillae are colored in between white, RHS N155A, and green-white, in between RHS 157C and 157D. Mature foliage, abaxial surface — In between green, RHS NN137A, and yellow-green, RHS 147A; fading lighter towards the base, nearest to RHS 143B, and greyed-green at the base, in between RHS 193C and 193D; outermost tip of the apex is greyed-red, in between RHS 180C and 180D; papillae are colored white, nearest to RHS N155A.

*Venation*.—No venation is visible.

*Petiole*.—No petiole; leaves are sessile.

Inflorescence: No flowering has been observed to date.

COMPARISONS WITH THE PARENT PLANT

Plants of the new cultivar 'AMIAL1614' differ from the parent, unnamed plant of *Aloe aristata*, in the following characteristics described in Table 1 below.

TABLE 1

| Characteristic | 'AMIAL1614' | unnamed plant of *Aloe aristata* |
|---|---|---|
| Leaf thickness. | Thicker and more robust than the parent. | Thinner and less robust than 'AMIAL1614'. |
| Leaf papillae. | Large, prominent papilla that are white in color; occasionally bearing spines; arranged in transverse rows on the abaxial leaf surface. | Papillae are less prominent. |
| Leaf width. | Approximately 2 times wider than the parent, giving the leaves a short appearance. | Narrow, giving the leaves a long and slender appearance. |

COMPARISONS WITH THE CLOSEST KNOWN COMPARATOR

Plants of the new cultivar 'AMIAL1614' differ from the commercial variety, *Aloe* 'Green Pearl' (not patented in the United States; European Union CPVO grant EU37467), in the following characteristics described in Table 2 below.

TABLE 2

| Characteristic | 'AMIAL1614' | 'Green Pearl' |
|---|---|---|
| Leaf width. | Approximately 1.5 times wider than 'Green Pearl'. | Narrower than 'AMIAL1614'. |
| Leaf thickness. | Thicker and more robust than 'Green Pearl'. | Thinner and less robust than 'AMIAL1614'. |
| General coloration of mature foliage. | Dark green. | Green to yellow green and suffused with greyed-green. |
| Leaf papillae. | Large, prominent papilla that are white in color and bearing spines in a distinct longitudinal row along the midrib of the abaxial surface; papilla are arranged in transverse rows on the abaxial leaf surface. | Papillae are smaller, less prominent, green-white in color, and occur randomly on the abaxial surface; none of the papilla bearing spines. |

That which is claimed is:

1. A new and distinct variety of *Aloe aristata* plant named 'AMIAL1614', substantially as described and illustrated herein.

* * * * *